(12) United States Patent
Ben-David et al.

(10) Patent No.: US 10,869,961 B2
(45) Date of Patent: Dec. 22, 2020

(54) LOCAL DISINFECTION FOR DRUG DELIVERY SYSTEM

(71) Applicant: SORREL MEDICAL LTD., Netanya (IL)

(72) Inventors: Ori Ben-David, Tel Aviv (IL); Andrei Yosef, Even Yehuda (IL); Shahar Zidon, Kibbutz Shefayim (IL); Michael Plaskin, Tirat-Carmel (IL)

(73) Assignee: SORREL MEDICAL LTD., Netanya (IL)

( * ) Notice: Subject to any disclaimer, the term of this patent is extended or adjusted under 35 U.S.C. 154(b) by 0 days.

(21) Appl. No.: 16/867,188

(22) Filed: May 5, 2020

(65) Prior Publication Data

US 2020/0261642 A1    Aug. 20, 2020

Related U.S. Application Data

(63) Continuation of application No. PCT/IL2018/051178, filed on Nov. 6, 2018, which is
(Continued)

(51) Int. Cl.
*A61L 2/10* (2006.01)
*A61L 2/04* (2006.01)
(Continued)

(52) U.S. Cl.
CPC .............. *A61M 5/001* (2013.01); *A61L 2/10* (2013.01); *A61L 2/24* (2013.01); *A61M 5/002* (2013.01);
(Continued)

(58) Field of Classification Search
CPC ................. A61M 5/001; A61L 2/10
See application file for complete search history.

(56) References Cited

U.S. PATENT DOCUMENTS

| 3,464,359 A | 9/1969 | King et al. |
| 6,355,024 B1 | 3/2002 | Small et al. |
| (Continued) | | |

FOREIGN PATENT DOCUMENTS

| EP | 3 050 585 B1 | 4/2019 |
| GB | 757116 A | 9/1956 |
| (Continued) | | |

OTHER PUBLICATIONS

U.S. Appl. No. 62/581,886, filed Nov. 7, 2017.
(Continued)

*Primary Examiner* — Donald R Spamer
(74) *Attorney, Agent, or Firm* — Sughrue Mion, PLLC

(57) ABSTRACT

Apparatus and a method are presented, including disinfecting a disinfection chamber that is defined between (i) a prefilled therapeutic substance reservoir and (ii) a sterile fluid path disposed within a therapeutic substance delivery device. The sterile fluid path includes a needle at an upstream end of the sterile fluid path and an injection assembly at a downstream end of the sterile fluid path. The disinfection occurs subsequently to the prefilled therapeutic substance reservoir being engaged with the therapeutic substance delivery device. Subsequently to disinfecting the disinfection chamber, the disinfection chamber and then the reservoir are penetrated with the needle. Other applications are also described.

20 Claims, 13 Drawing Sheets

Related U.S. Application Data a continuation-in-part of application No. 15/872,552, filed on Jan. 16, 2018.

(60) Provisional application No. 62/581,886, filed on Nov. 6, 2017.

(51) Int. Cl.
  *A61L 2/16* (2006.01)
  *A61M 5/00* (2006.01)
  *A61M 5/142* (2006.01)
  *A61M 5/162* (2006.01)
  *A61M 5/14* (2006.01)
  *A61L 2/24* (2006.01)

(52) U.S. Cl.
  CPC ...... *A61M 5/1408* (2013.01); *A61M 5/14248* (2013.01); *A61M 5/162* (2013.01); *A61L 2202/11* (2013.01); *A61L 2202/122* (2013.01); *A61L 2202/14* (2013.01); *A61L 2202/24* (2013.01)

(56) References Cited

U.S. PATENT DOCUMENTS

| | | |
|---|---|---|
| 6,645,171 B1 | 11/2003 | Robinson et al. |
| 7,740,619 B2 | 6/2010 | Pinedjian et al. |
| 7,931,859 B2 | 4/2011 | Mlodzinski et al. |
| 8,431,074 B2 | 4/2013 | Neer |
| 8,540,693 B2 | 9/2013 | Arnitz et al. |
| 8,779,386 B2 | 7/2014 | Bak |
| 9,604,740 B2 | 3/2017 | Py |
| 9,677,555 B2 | 6/2017 | Kamen et al. |
| 9,901,651 B2 | 2/2018 | Finke et al. |
| 2009/0036868 A1 | 2/2009 | Pinedjian et al. |
| 2013/0177455 A1 | 7/2013 | Kamen et al. |
| 2015/0265735 A1 | 9/2015 | Ma |
| 2015/0352297 A1 | 12/2015 | Stedman et al. |
| 2016/0038666 A1 | 2/2016 | Kelly et al. |
| 2016/0354555 A1 | 12/2016 | Gibson et al. |
| 2017/0182242 A1 | 6/2017 | Galitz et al. |
| 2019/0111202 A1* | 4/2019 | Falkovich ................ A61L 2/10 |
| 2019/0134295 A1 | 5/2019 | Plaskin et al. |
| 2019/0351143 A1 | 11/2019 | Egloff et al. |
| 2019/0365993 A1 | 12/2019 | Staub et al. |

FOREIGN PATENT DOCUMENTS

| | | |
|---|---|---|
| WO | 2008/024810 A2 | 2/2008 |
| WO | 2008/133702 A1 | 11/2008 |
| WO | 2011/133823 A1 | 10/2011 |
| WO | 2012/108955 A2 | 8/2012 |
| WO | 2014/090745 A1 | 6/2014 |
| WO | 2014/191038 A1 | 12/2014 |
| WO | 2015/032747 A1 | 3/2015 |
| WO | 2015/061386 | 4/2015 |
| WO | 2015/061386 A1 | 4/2015 |
| WO | 2016/141082 | 9/2016 |
| WO | 2016/141082 A1 | 9/2016 |
| WO | 2018/141697 A1 | 8/2018 |
| WO | 2019/087198 | 5/2019 |

OTHER PUBLICATIONS

An International Search Report and a Written Opinion both dated Mar. 21, 2019, which issued during the prosecution of Applicant's PCT/IL2018/051178.

An Office Action dated Apr. 13, 2020, which issued during the prosecution of U.S. Appl. No. 15/872,552.

International Search Report of PCT/IL2018/051178 dated Mar. 21, 2019 [PCT/ISA/210].

Written Opinion of PCT/IL2018/051178 dated Mar. 21, 2019 [PCT/ISA/237].

* cited by examiner

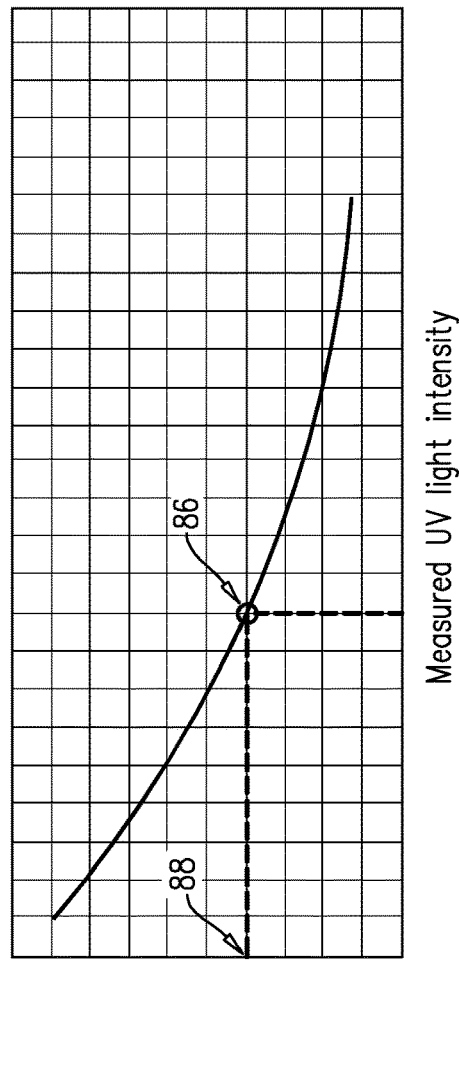
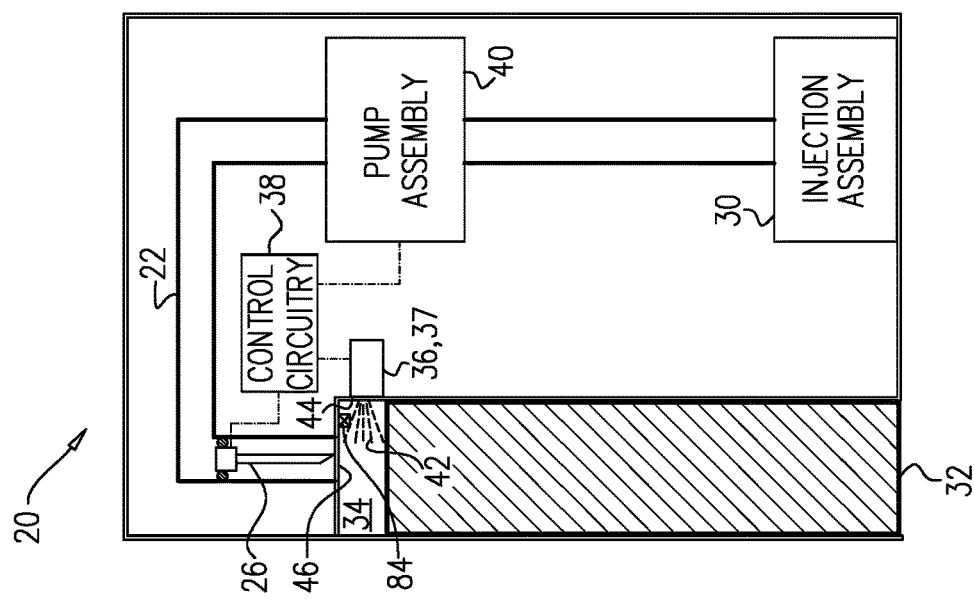
FIG. 4B
FIG. 4A

LOCAL DISINFECTION FOR DRUG DELIVERY SYSTEM

CROSS-REFERENCES TO RELATED APPLICATIONS

The present application is a Continuation of PCT/IL2018/051178 to Ben-David, which published as WO 2019/087198 and:

(a) claims priority from U.S. Application No. 62/581,886 to Plaskin, filed Nov. 6, 2017, entitled, "Local disinfection for prefilled drug delivery system," and (b) claims priority from and is a continuation-in-part of U.S. application Ser. No. 15/872,552 to Plaskin, filed Jan. 16, 2018, entitled, "Local disinfection for prefilled drug delivery system," which published as US 2019/0134295 to Plaskin and which claims priority from U.S. Application No. 62/581,886 to Plaskin, filed Nov. 6, 2017.

Each of the above-referenced applications is assigned to the assignee of the present application and is incorporated herein by reference.

FIELD OF THE INVENTION

The present invention relates generally to delivery of a therapeutic substance to a subject, and more specifically to wearable drug delivery devices utilizing therapeutic substance reservoirs.

BACKGROUND

Pumps are often used in the medical industry for delivering therapeutic substances, e.g., drugs, to subjects. Therapeutic substances such as saline solution, insulin, antibiotics, chemotherapy drugs, and biosimilar drugs may all be delivered to a subject with medical pumps. Some medical pumps utilize therapeutic substance reservoirs that are prefilled by a pharmaceutical company. The medical pumps may be manufactured in a controlled environment and subsequently sterilized, and the therapeutic substance reservoirs may be prefilled in a sterile environment. When engaging a medical pump with a prefilled therapeutic substance reservoir, bacteria or viruses may be introduced into the engagement site.

SUMMARY OF THE INVENTION

Apparatus, such as for example a wearable medical patch pump, is provided for use with a prefilled therapeutic substance reservoir, such that after engaging the pump with the reservoir, the engagement site between the pump and the reservoir is disinfected prior to fluid communication between the pump and the reservoir being established. The patch pump is designed such that engagement between the prefilled therapeutic substance reservoir and the pump defines a closed chamber between the reservoir and a sterile fluid path within the pump, referred to hereinbelow as a disinfection chamber. After the pump and reservoir have been engaged, the disinfection chamber is disinfected. Subsequently a needle from within the pump penetrates through the disinfection chamber and into the reservoir in order to establish fluid communication between the pump and the reservoir. Fluid communication between the reservoir and the sterile fluid path is thereby established with reduced risk of potentially harmful bacteria coming in to contact with the therapeutic substance. Typically, the reservoir does not have to be disinfected prior to engagement with the pump, e.g., by swabbing with alcohol, nor does engagement of the reservoir and the pump have to occur while the reservoir and the fluid path are contained within a sterile environment.

There is therefore provided, in accordance with some applications of the present invention, a method including:

disinfecting a disinfection chamber that is defined between (i) a prefilled therapeutic substance reservoir and (ii) a sterile fluid path disposed within a therapeutic substance delivery device, the sterile fluid path including a needle at an upstream end of the sterile fluid path and an injection assembly at a downstream end of the sterile fluid path; and subsequently, penetrating the disinfection chamber and then the reservoir with the needle.

For some applications, the step of disinfecting the disinfection chamber is performed following a user of the therapeutic substance delivery device engaging the prefilled therapeutic substance reservoir with the therapeutic substance delivery device, the disinfection chamber being defined when the prefilled therapeutic substance reservoir becomes engaged with the therapeutic substance delivery device.

For some applications, the step of disinfecting the disinfection chamber is performed following a user of the therapeutic substance delivery device removing the therapeutic substance delivery device from commercial packaging, the prefilled therapeutic substance reservoir and the therapeutic substance delivery device being engaged with one another inside the commercial packaging.

For some applications, disinfecting the disinfection chamber includes activating a disinfection assembly and subsequently terminating the activation of the disinfection assembly, and penetrating the disinfection chamber includes penetrating the disinfection chamber within 10 seconds after terminating the activation of the disinfection assembly.

For some applications, disinfecting the disinfection chamber includes activating a disinfection assembly and terminating activation of the disinfection assembly within 5 minutes after activating the disinfection assembly.

For some applications, disinfecting the disinfection chamber includes irradiating the disinfection chamber with ultraviolet radiation.

For some applications, irradiating the disinfection chamber includes irradiating the disinfection chamber with ultraviolet radiation at a power level of 1-200 mW.

For some applications, irradiating the disinfection chamber includes irradiating the disinfection chamber with ultraviolet radiation at a wavelength of 100-400 nm.

For some applications, irradiating the disinfection chamber with the ultraviolet radiation includes irradiating the disinfection chamber with ultraviolet radiation at a plurality of wavelengths.

For some applications, irradiating the disinfection chamber includes irradiating the disinfection chamber with ultraviolet light using an ultraviolet light emitting diode.

For some applications, the method further includes:

subsequently to irradiating the disinfection chamber with the ultraviolet light, measuring a value indicative of intensity of the ultraviolet radiation within the disinfection chamber; and terminating the irradiation of the disinfection chamber at a time determined based on the measured value.

For some applications, measuring the value indicative of intensity of the ultraviolet radiation includes measuring the intensity of the ultraviolet radiation within the disinfection chamber using an ultraviolet sensor disposed within the disinfection chamber.

For some applications, (a) irradiating the disinfection chamber with ultraviolet radiation includes activating an ultraviolet light emitting diode (UV LED) and (b) measuring the value indicative of intensity of the ultraviolet radiation includes measuring a current input to the UV LED.

For some applications, disinfecting the disinfection chamber includes heating the disinfection chamber.

For some applications, heating the disinfection chamber includes heating the disinfection chamber to a temperature of 40-70 degrees Celsius.

For some applications, heating the disinfection chamber includes heating the disinfection chamber to a temperature of 70-300 degrees Celsius.

For some applications, disinfecting the disinfection chamber includes releasing a disinfectant fluid into the disinfection chamber.

For some applications, disinfecting the disinfection chamber includes disinfecting the disinfection chamber within 5 minutes prior to penetrating the disinfection chamber and subsequently the reservoir with the needle.

For some applications, disinfecting the disinfection chamber includes disinfecting the disinfection chamber at least 1 month following engagement of the prefilled therapeutic substance reservoir with the therapeutic substance delivery device.

For some applications, disinfecting the disinfection chamber includes disinfecting the disinfection chamber at least 6 months following engagement of the prefilled therapeutic substance reservoir with the therapeutic substance delivery device.

For some applications, the disinfecting of the disinfection chamber is at least a second disinfecting of the disinfection chamber, a first disinfecting of the disinfection chamber occurring prior to the therapeutic substance delivery device being packaged for commercial sale.

For some applications, the method further includes disinfecting the disinfection chamber at least one time between the first disinfecting of the disinfection chamber and the at least a second disinfecting of the disinfection chamber.

There is further provided, in accordance with some applications of the present invention, apparatus for delivering a therapeutic substance to a subject, the apparatus including:
a therapeutic substance delivery device:
  (a) including a sterile fluid path for delivering the therapeutic substance to the subject, the sterile fluid path including a needle at an upstream end of the sterile fluid path and an injection assembly at a downstream end of the sterile fluid path, and
  (b) configured to engage with a prefilled therapeutic substance reservoir, such that when the therapeutic substance delivery device and the reservoir are engaged with one another a disinfection chamber is defined between the sterile fluid path and the reservoir, the needle being configured to penetrate the disinfection chamber and subsequently the reservoir when the therapeutic substance delivery device and the reservoir are engaged with one another, such that fluid communication is established between the reservoir and the sterile fluid path;
a disinfection assembly disposed within the therapeutic substance delivery device and configured to disinfect the disinfection chamber prior to the needle penetrating the disinfection chamber; and
control circuitry configured to (a) activate the disinfection assembly, (b) terminate the activation of the disinfection assembly, and subsequently (c) drive the needle to penetrate the disinfection chamber and subsequently the reservoir.

For some applications, the control circuitry is configured to terminate the activation of the disinfection assembly within 5 minutes after activating the disinfection assembly.

For some applications, the control circuitry is configured to drive the needle to penetrate the disinfection chamber within 10 seconds after terminating the activation of the disinfection assembly.

For some applications, a surface area of the disinfection chamber is 1-400 mm2.

For some applications, the disinfection assembly includes an ultraviolet radiation source that is configured to emit ultraviolet radiation, and the control circuitry is configured to activate the ultraviolet radiation source to irradiate the disinfection chamber.

For some applications, the ultraviolet radiation source is configured to emit the ultraviolet radiation at a power level of 1-200 mW.

For some applications, the ultraviolet radiation source is configured to emit the ultraviolet radiation at a wavelength of 100-400 nm.

For some applications, the ultraviolet radiation source is configured to emit the ultraviolet radiation at a plurality of wavelengths.

For some applications, the ultraviolet radiation source includes an ultraviolet light emitting diode.

For some applications, at least one surface of the disinfection chamber is a reflective surface configured to reflect the ultraviolet radiation.

For some applications, the reflective surface is configured to reflect at least 10% of the ultraviolet radiation.

For some applications, the reflective surface includes expanded polytetrafluoroethylene (ePTFE).

For some applications, the reflective surface includes aluminum.

For some applications, the reflective surface of the disinfection chamber is configured to focus the ultraviolet radiation to a designated area within the disinfection chamber, the designated area being within 3 mm of where the needle penetrates the reservoir.

For some applications:
  the apparatus further includes a sensor configured to measure a value indicative of intensity of the ultraviolet radiation within the disinfection chamber, and
  the control circuitry is configured to (a) activate the ultraviolet radiation source, (b) receive the value indicative of the intensity of the ultraviolet radiation, (c) terminate the activation of the ultraviolet radiation source at a time determined based on the measured value, and subsequently (d) drive the needle to penetrate the disinfection chamber and subsequently the reservoir.

For some applications, the control circuitry is configured to (a) activate the ultraviolet radiation source, (b) measure a current input to the ultraviolet radiation source, the current being indicative of intensity of the ultraviolet radiation within the disinfection chamber, (c) terminate the activation of the ultraviolet radiation source at a time determined based on the measured current, and subsequently (d) drive the needle to penetrate the disinfection chamber and subsequently the reservoir.

For some applications, the ultraviolet radiation source includes an ultraviolet light emitting diode (UV LED), and the control circuitry is configured to measure a current input to the UV LED.

For some applications, the disinfection assembly includes a heat source and the control circuitry is configured to activate the heat source to heat the disinfection chamber.

For some applications, the control circuitry is configured to activate the heat source to heat the disinfection chamber to a temperature of 40-70 degrees Celsius.

For some applications, the control circuitry is configured to activate the heat source to heat the disinfection chamber to a temperature of 70-300 degrees Celsius.

For some applications, the control circuitry is configured to (a) activate the heat source, (b) measure a current input to the heat source, the current being indicative of temperature of the disinfection chamber, (c) terminate the activation of the heat source at a time determined based on the measured current, and subsequently (d) drive the needle to penetrate the disinfection chamber and then the reservoir.

For some applications:

the apparatus further includes a temperature sensor disposed within the disinfection chamber and configured to measure a temperature of the disinfection chamber, and the control circuitry is configured to (a) activate the heat source, (b) receive a value from the temperature sensor of the temperature of the disinfection chamber, (c) terminate the activation of the heat source at a time determined based on the measured temperature, and subsequently (d) drive the needle to penetrate the disinfection chamber and then the reservoir.

For some applications, the disinfection assembly includes a disinfectant fluid reservoir containing disinfectant fluid, and the control circuitry is configured to activate the disinfectant fluid assembly to release the disinfectant fluid from the disinfectant fluid reservoir into the disinfection chamber.

For some applications, the control circuitry is further configured to activate the therapeutic substance delivery device to deliver the therapeutic substance to the subject.

For some applications, the apparatus is packaged for commercial sale with the therapeutic substance delivery device and the reservoir engaged with one another.

For some applications, the control circuitry is configured to sequentially (a) activate the disinfection assembly a first time prior to the apparatus being packaged for commercial sale, (b) terminate the activation of the disinfection assembly, (c) activate the disinfection assembly at least a second time at least 1 month following the apparatus being packaged for commercial sale, (d) terminate the activation of the disinfection assembly, and (e) drive the needle to penetrate the disinfection chamber and subsequently the reservoir.

For some applications, the control circuitry is configured to activate the disinfection assembly the at least a second time at least 6 months following the apparatus being packaged for commercial sale.

For some applications, the apparatus is packaged for commercial sale with the therapeutic substance delivery device and the prefilled therapeutic substance reservoir, the therapeutic substance delivery device and the prefilled therapeutic substance reservoir not being engaged with one another.

For some applications, the apparatus is packaged for commercial sale without the prefilled therapeutic substance reservoir.

For some applications, the sterile fluid path is a first sterile fluid path and the needle is a first needle, the therapeutic substance delivery device:

(a) further including a second sterile fluid path, the second sterile fluid path including a second needle at an upstream end of the second sterile fluid path and the injection assembly at a downstream end of the second fluid path, (b) further configured to engage with a second prefilled therapeutic substance reservoir, such that when the first and second reservoirs are engaged with the therapeutic substance delivery device first and second disinfection chambers are defined respectively (i) between the first sterile fluid path and the first reservoir, and (ii) between the second sterile fluid path and the second reservoir, (c) further including a first sterile fluid path valve disposed between the first needle and the injection assembly and configured to control fluid communication between the first reservoir and the injection assembly, and (d) further including a second sterile fluid path valve disposed between the second needle and the injection assembly and configured to control fluid communication between the second reservoir and the injection assembly, the first and second needles being configured to penetrate the first and second disinfection chambers respectively and subsequently the first and second reservoirs respectively when the therapeutic substance delivery device is engaged with the first and second reservoirs, such that a first fluid communication is established between the first sterile fluid path and the first reservoir and a second fluid communication is established between the second sterile fluid path and the second reservoir, and the disinfection assembly being configured to (a) disinfect the first disinfection chamber prior to the first needle penetrating the first disinfection chamber, and (b) disinfect the second disinfection chamber prior to the second needle penetrating the second disinfection chamber.

For some applications, the disinfection assembly is a first disinfection assembly configured to disinfect the first disinfection chamber, the apparatus further includes a second disinfection assembly configured to disinfect the second disinfection chamber, and the control circuitry is configured to activate the first and second disinfection assemblies.

For some applications:

(a) the needle is a first needle and the sterile fluid path further includes a second needle at the upstream end of the sterile fluid path, (b) when the therapeutic substance delivery device and the reservoir are engaged with one another the first and second needles are configured to penetrate the disinfection chamber and subsequently the reservoir such that fluid communication is established between the reservoir and the sterile fluid path via the first and second needles, and (c) the control circuitry is configured to drive the first and second needles to penetrate the disinfection chamber, within 10 seconds after terminating the activation of the disinfection assembly.

The present invention will be more fully understood from the following detailed description of applications thereof, taken together with the drawings, in which:

BRIEF DESCRIPTION OF THE DRAWINGS

FIG. 4A is a schematic illustrations of a therapeutic substance delivery device that includes a disinfection assembly, and a sensor disposed within a disinfection chamber;

FIG. 4B is a graph showing a model that may be used to determine disinfection time based on measurements taken by the sensor of FIG. 4A, in accordance with some applications of the present invention.

DETAILED DESCRIPTION

Figure 1A:
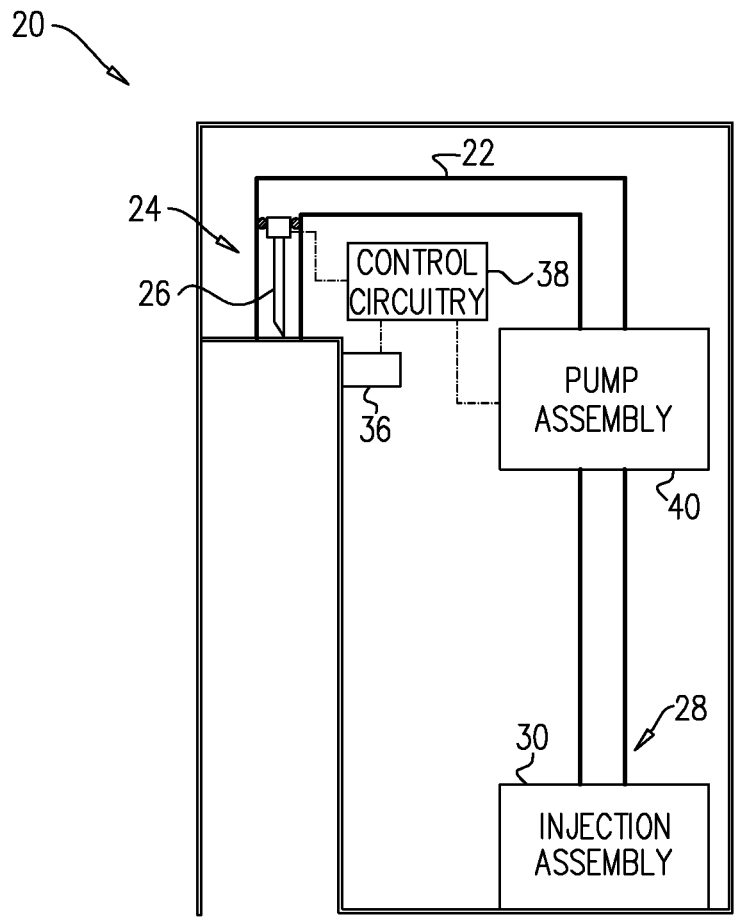
FIG. 1A is a schematic illustration of a therapeutic substance delivery device that includes a disinfection assembly and is configured to engage with a prefilled therapeutic substance reservoir, the reservoir being shown outside the therapeutic substance delivery device, in accordance with some applications of the present invention.
Figure 1A:
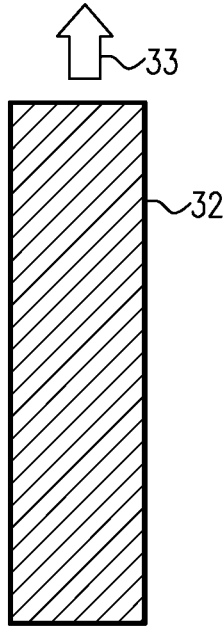
Figure 1B:
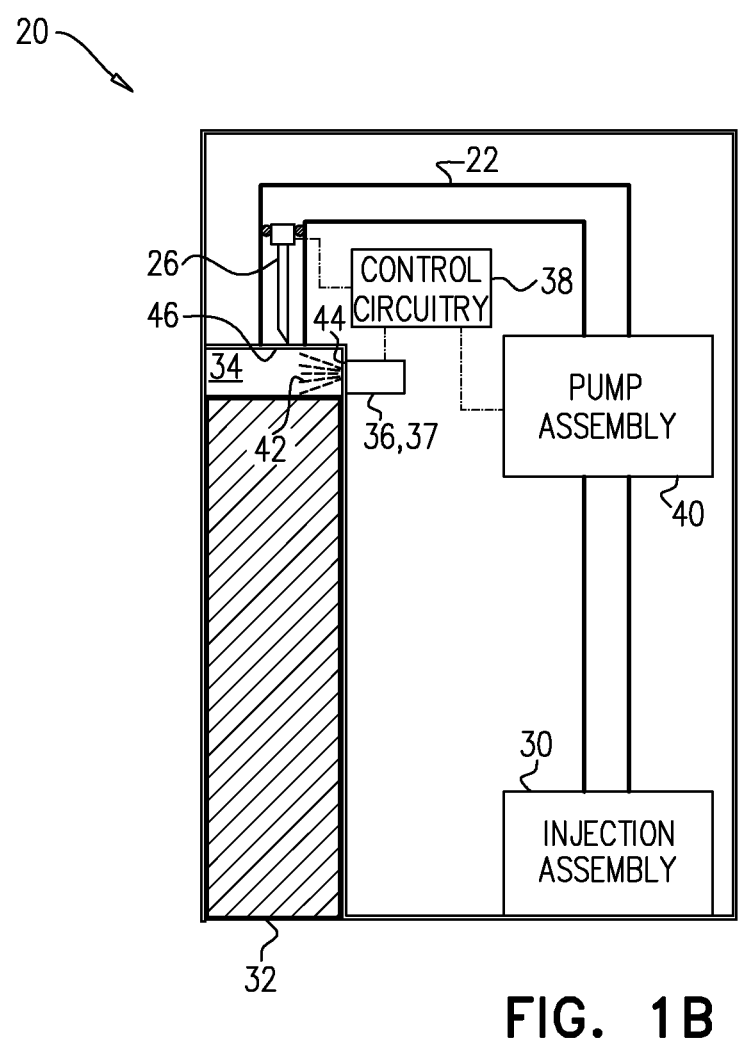
FIG. 1B is a schematic illustration of the therapeutic substance delivery device of FIG. 1A with the prefilled therapeutic substance reservoir shown engaged with the therapeutic substance delivery device, in accordance with some applications of the present invention.
Figure 1C:
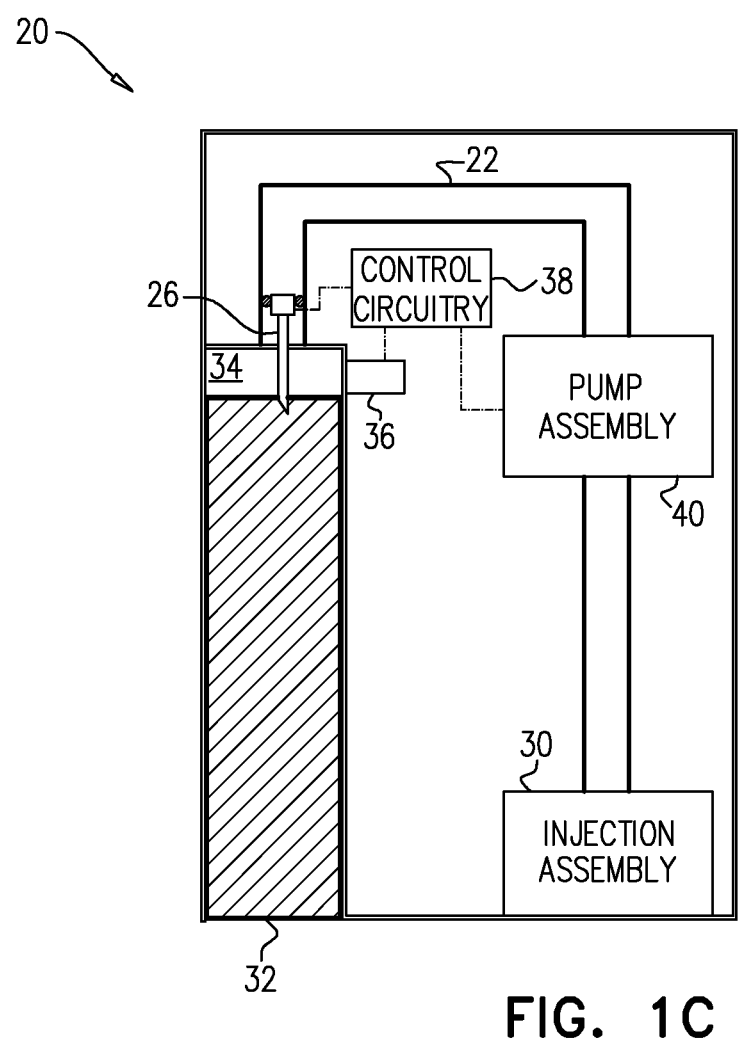
FIG. 1C is a schematic illustration of the therapeutic substance delivery device of FIGS. 1A-B, showing establishment of fluid communication by penetration of the reservoir with a needle, in accordance with some applications of the present invention.

Reference is now made to FIGS. 1A-C, which are schematic illustrations of a therapeutic substance delivery device 20 configured to engage with a therapeutic substance reservoir 32, e.g., a prefilled therapeutic substance reservoir 32, in accordance with some applications of the present invention. Within therapeutic substance delivery device 20 is a sterile fluid path 22 for delivering therapeutic substance to a subject. Sterile fluid path 22 has a needle 26 at an upstream end 24 of sterile fluid path 22, and an injection assembly 30 at a downstream end 28 of sterile fluid path 22. Therapeutic substance delivery device 20 and prefilled therapeutic substance reservoir 32 are configured to engage with one another, such as is shown by arrow 33 in FIG. 1A, e.g., reservoir 32 is configured to be inserted into therapeutic substance delivery device 20. When therapeutic substance delivery device 20 and reservoir 32 are engaged with one another, such as is shown in FIG. 1B, a sealed disinfection chamber 34 is defined between sterile fluid path 22 and reservoir 32. While therapeutic substance delivery device 20 and reservoir 32 are typically sterile, disinfection chamber 34 is (a) initially non-sterile, and (b) typically sealed from further bacteria or virus penetration. Needle 26 may be driven to penetrate disinfection chamber 34 and subsequently reservoir 32 when therapeutic substance delivery device 20 and reservoir 32 are engaged with one another, such that fluid communication is established between reservoir 32 and sterile fluid path 22, such as is shown in FIG. 1C.

Disposed within therapeutic substance delivery device 20 is a disinfection assembly 36 that disinfects disinfection chamber 34 prior to needle 26 penetrating disinfection chamber 34. Typically, control circuitry 38 activates disinfection assembly 36, terminates the activation of disinfection assembly 36 after disinfection chamber 34 has been disinfected, and then drives needle 26 to penetrate disinfection chamber 34 and subsequently reservoir 32. Once fluid communication is established between reservoir 32 and sterile fluid path 22, control circuitry 38 drives a pump assembly 40 to draw therapeutic substance from reservoir 32 and deliver it to the subject via injection assembly 30.

Typically, in order to decrease the amount of time spent disinfecting, disinfection chamber 34 is small. For example, a total surface area of disinfection chamber 34 may be at least 1 mm2 and/or less than 400 mm2. Disinfection can therefore typically occur within 5 minutes, e.g., within 10 seconds. Control circuitry 38 is typically configured to terminate the activation of disinfection assembly 36 within 5 minutes, e.g., within 10 seconds, after activating disinfection assembly 36.

Local disinfection of the engagement site between reservoir 32 and therapeutic substance delivery device 20 from inside the delivery device allows for (a) engagement of reservoir 32 and therapeutic substance delivery device 20 to occur substantially prior to therapeutic substance delivery device 20 being used to deliver the therapeutic substance to a subject, while (b) disinfection of the engagement site may not occur until moments before delivery of the therapeutic substance. For example, prefilled therapeutic substance reservoir 32 may be inserted into therapeutic substance delivery device 20 up to 3 years prior to therapeutic substance delivery device 20 being used for delivery of a therapeutic substance.

For some applications, once attached to a subject, a user control may be used to activate control circuitry 38. In response to activation by the user control, control circuitry 38 (a) activates disinfection assembly 36 such that disinfection chamber 34 is disinfected, (b) terminates the activation of disinfection assembly 36 within 5 minutes after activating disinfection assembly 36, and (c) drives needle 26 to penetrate disinfection chamber 34 within 10 seconds after terminating the activation of disinfection assembly 36. Thus, disinfecting of disinfection chamber 34 typically occurs within 5 minutes prior to penetrating disinfection chamber 34 and then reservoir 32 with needle 26.

Additionally, local disinfection of the engagement site that (a) occurs inside the delivery device after the engagement, and (b) is activated by control circuitry 38, reduces, in a way that is automated and integrated into therapeutic substance delivery device 20, a risk of potentially harmful bacteria or viruses coming in to contact with the therapeutic substance. Typically, reservoir 32 does not have to be disinfected prior to engagement with therapeutic substance delivery device 20, e.g., by swabbing reservoir 32 with alcohol, nor does engagement of the reservoir and the therapeutic substance delivery device have to occur while the reservoir and the fluid path are contained within a sterile environment.

For some applications, the apparatus may be packaged for commercial sale with therapeutic substance delivery device 20 and prefilled therapeutic substance reservoir 32 already engaged with one another and configured for use typically within 3 years. Typically, therapeutic substances used in patch pumps have a shelf-life of up to around 3 years. Thus, the disinfecting of disinfection chamber 34 within 5 minutes prior to needle 26 penetrating disinfection chamber 34 may occur up to 3 years, e.g., at least 1 month, e.g., at least 6 months, following engagement of therapeutic substance reservoir 32 with therapeutic substance delivery device 20.

For some applications, a first disinfecting of disinfection chamber 34 may occur prior to therapeutic substance delivery device 20 being packaged for commercial sale, which helps to reduce bacterial growth within disinfection chamber during shelf-life. Thus, the disinfecting of disinfection chamber 34 that occurs within 5 minutes prior to needle 26 penetrating disinfection chamber 34 and then reservoir 32 may be at least a second disinfecting, e.g., occurring at least 1 month (e.g., at least 6 months, e.g., up to 3 years) following the first disinfecting of disinfection chamber 34 that occurs prior to therapeutic substance delivery device 20 being packaged for commercial sale. For some applications, disinfecting disinfection chamber 34 may also occur intermittently during the shelf-life of therapeutic substance delivery device 20, i.e., at least one time between the first disinfecting of disinfection chamber 34 (prior to commercial packaging) and the second disinfecting of disinfection chamber 34 (within 5 minutes prior to penetration by needle 26).

For some applications, therapeutic substance delivery device 20 may be packaged for commercial sale along with prefilled therapeutic substance reservoir 32, but without therapeutic substance delivery device 20 and reservoir 32 being already engaged. Alternatively, therapeutic substance delivery device 20 may be packaged for commercial sale on its own, without prefilled therapeutic substance reservoir 32.

For some applications, disinfection assembly 36 is an ultraviolet radiation source 37 (FIG. 1B), e.g., an ultraviolet light emitting diode (UV LED), that is configured to irradiate disinfection chamber 34 by emitting ultraviolet radiation 42 inside disinfection chamber 34. For some applications, the UV LED may be mounted within therapeutic substance delivery device 20 such that only the actual diode of the UV LED is inside disinfection chamber 34, while other electronic components associated with the UV LED are outside of disinfection chamber 34 and connected to control circuitry 38. For example, there may be a small hole in disinfection chamber 34 through which the UV LED or associated electronic components are sealably disposed. Ultraviolet radiation source 37 is typically configured to emit ultraviolet radiation 42 at a wavelength of at least 100 nm and/or less than 400 nm. Ultraviolet radiation source 37 may be configured to emit ultraviolet radiation 42 at a plurality of wavelengths.

For some applications, at least one surface of disinfection chamber 34, such as surface 46, is a reflective surface configured to reflect ultraviolet radiation 42. For example, surface 46 may be configured to reflect at least 10% of ultraviolet radiation 42. For some applications, reflective surface 46 may be expanded polytetrafluoroethylene (ePTFE) or aluminum. Surface 46 being reflective and disinfection chamber 34 being small, as described hereinabove, may independently and/or in combination allow for the disinfection assembly 36 to operate on low power. Typically, ultraviolet radiation source 37 is configured to emit ultraviolet radiation 42 at a power level of less than 200 mW.

Figure 1D:
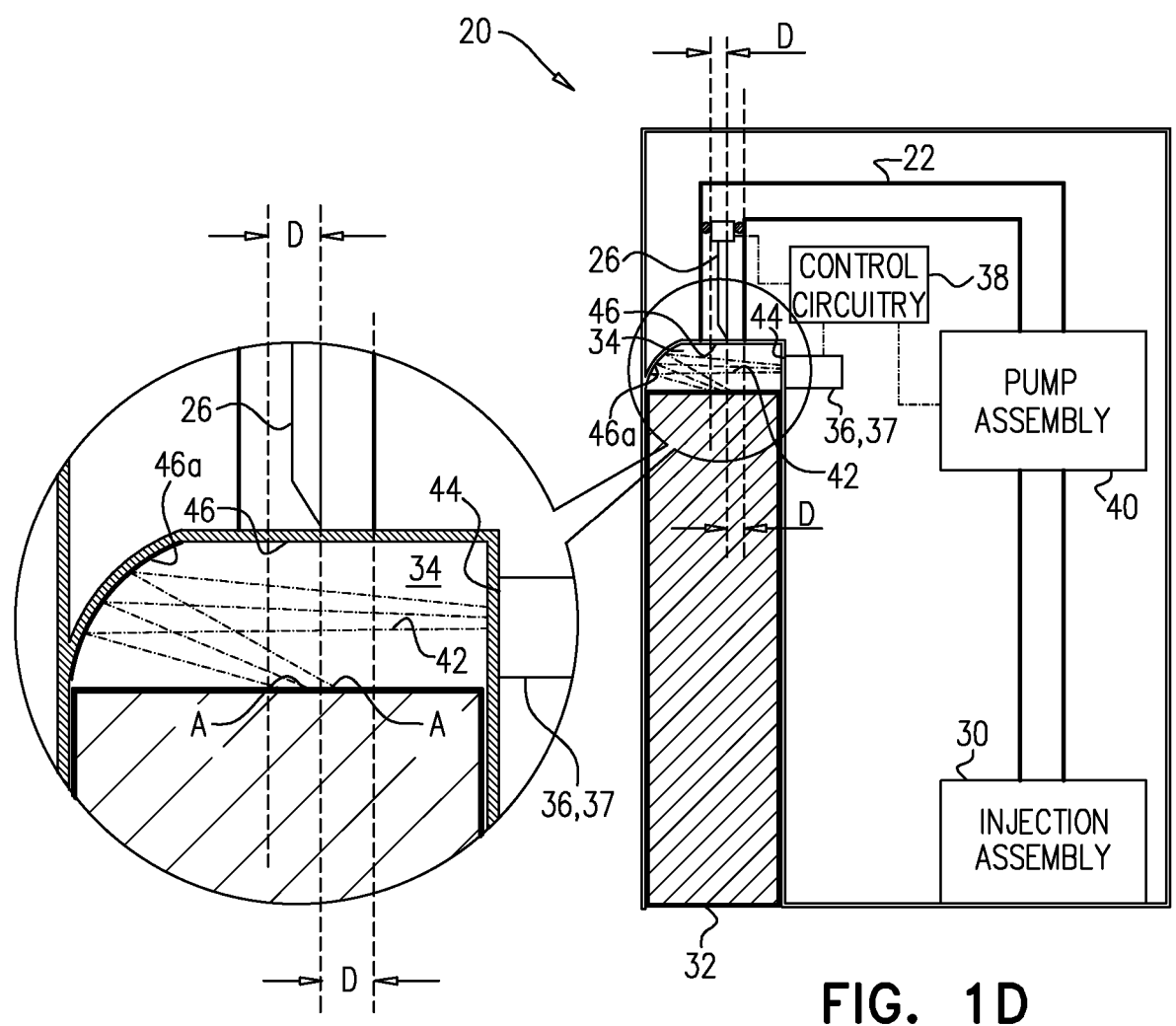
FIG. 1D is a schematic illustration of a therapeutic substance delivery device that includes a disinfection assembly, showing a reflective surface within a disinfection chamber, in accordance with some applications of the present invention.

Reference is now made to FIG. 1D, which is a schematic illustration of therapeutic substance delivery device 20 showing a reflective surface 46a within a disinfection chamber, in accordance with some applications of the present invention. For some applications, the reflective surface of disinfection chamber 34 may be a curved reflective surface 46a that focuses the ultraviolet radiation to a designated area A that is, for example, within a 3 mm distance D of where needle 26 penetrates therapeutic substance reservoir 32. For example, curved surface 46a may be configured to reflect at least 10% of ultraviolet radiation 42 toward designated area A. Focusing the ultraviolet radiation to a small area surrounding the penetration point on therapeutic substance reservoir 32 increases the efficacy of the disinfection around the penetration point. For some applications, reflective surface 46a may be expanded polytetrafluoroethylene (ePTFE) or aluminum. For some applications, more than one surface of disinfection chamber 34 may be reflective, for example, surface 46 and surface 46a may both be configured to reflect ultraviolet radiation 42.

For some applications, disinfection assembly 36 is a heat source. When activated by control circuitry 38, the heat source disinfects disinfection chamber 34 by heating disinfection chamber 34 to a temperature of at least 40 degrees Celsius and/or less than 300 degrees Celsius, e.g., 70 degrees Celsius. Alternatively or additionally, disinfection assembly 36 is a disinfectant fluid reservoir that contains disinfectant fluid. When activated by control circuitry 38, the disinfectant fluid assembly releases the disinfectant fluid, e.g., sprays the disinfectant fluid, from the disinfectant fluid reservoir into disinfection chamber 34.

Figure 2A:
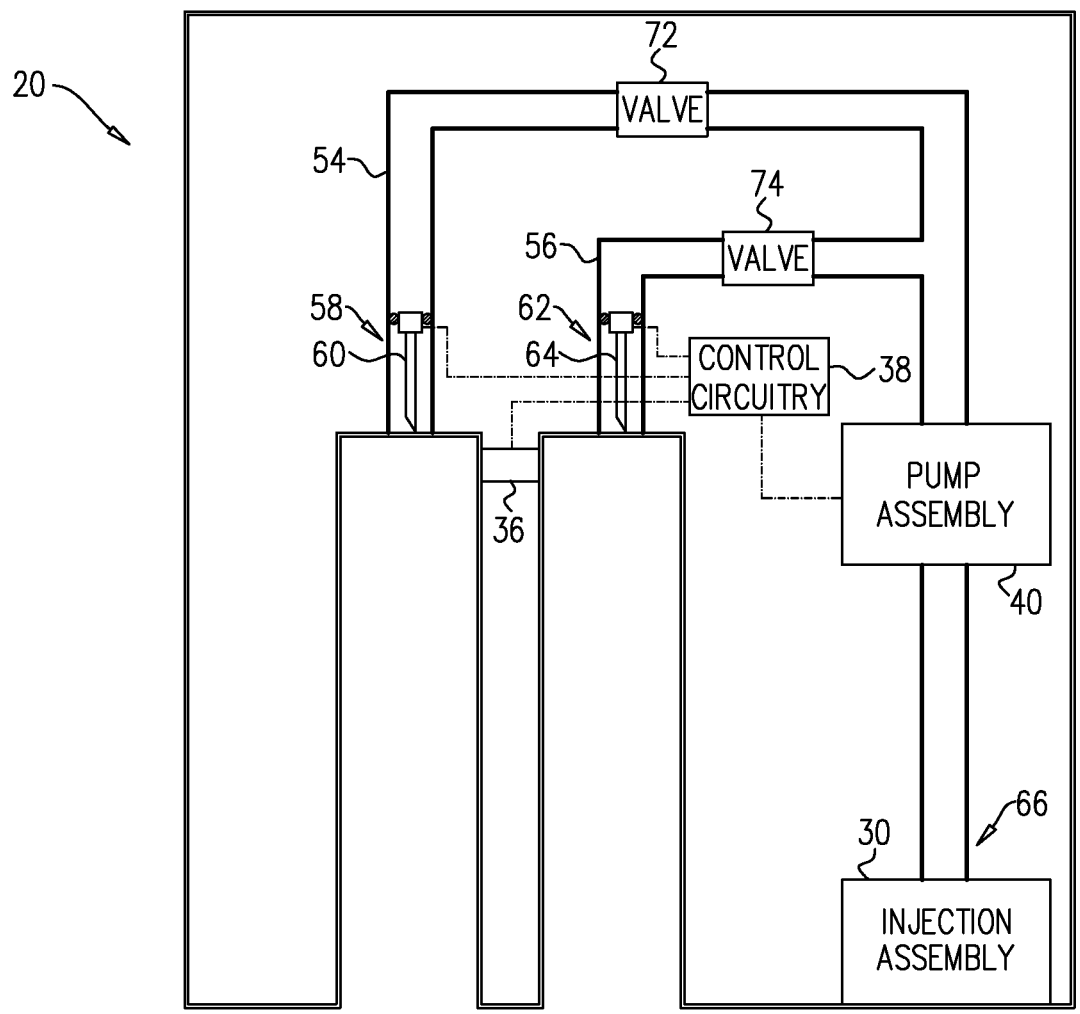
FIG. 2A is a schematic illustration of a therapeutic substance delivery device that includes a disinfection assembly and is configured to engage with two prefilled therapeutic substance reservoirs, the reservoirs being shown outside the therapeutic substance delivery device, in accordance with some applications of the present invention.
Figure 2B:
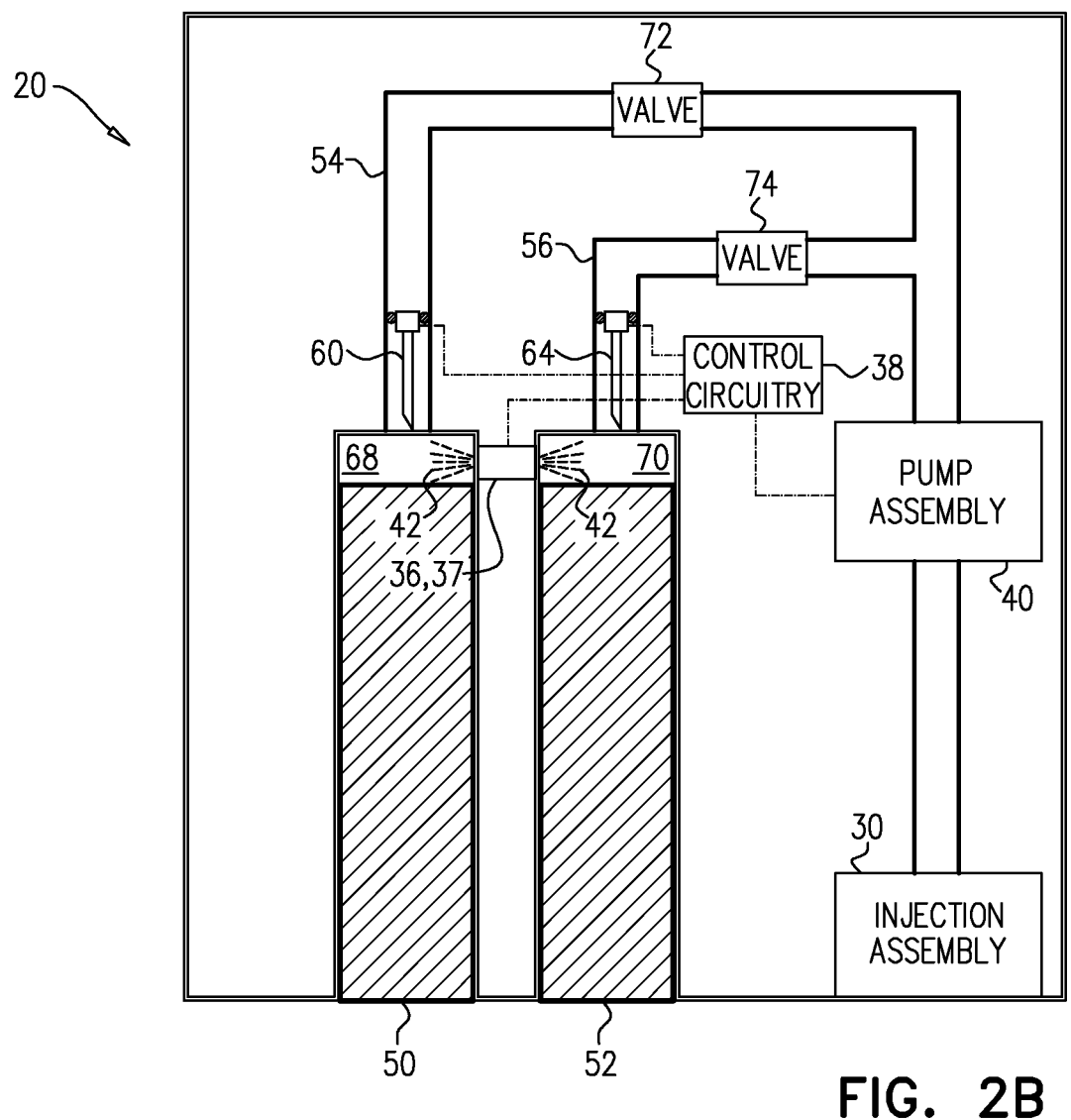
FIG. 2B is a schematic illustration of the therapeutic substance delivery device of FIG. 2A with the prefilled therapeutic substance reservoirs shown engaged with the therapeutic substance delivery device, in accordance with some applications of the present invention.
Figure 2C:
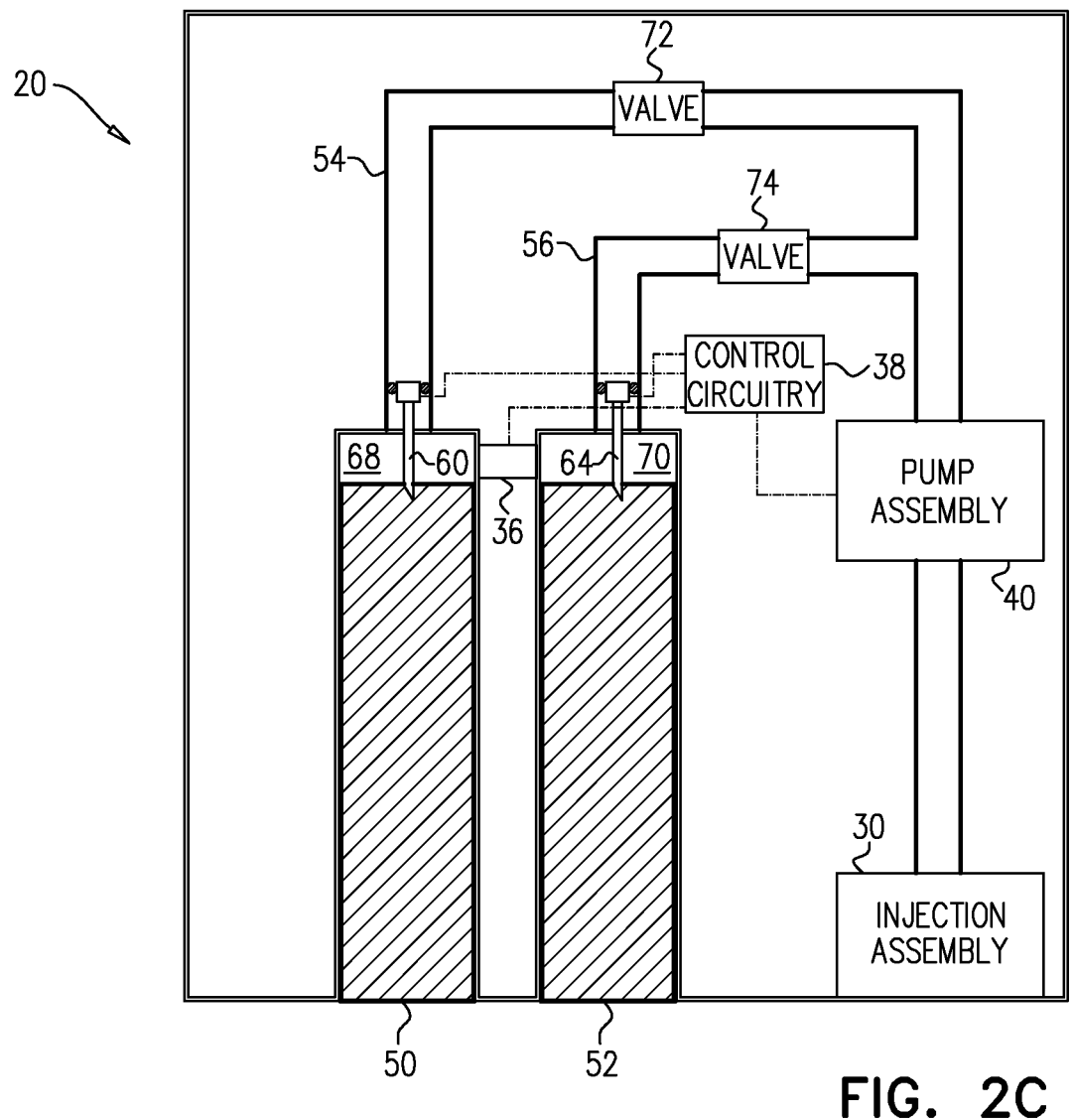
FIG. 2C is a schematic illustration of the therapeutic substance delivery device of FIGS. 2A-B showing establishment of fluid communication by penetration of the reservoirs with respective needles, in accordance with some applications of the present invention.

Reference is now made to FIGS. 2A-C, which are schematic illustrations of therapeutic substance delivery device 20 configured to engage with a first prefilled therapeutic substance reservoir 50 and a second prefilled therapeutic substance reservoir 52, in accordance with some applications of the present invention. For some applications, therapeutic substance delivery device 20 has a first sterile fluid path 54 and a second sterile fluid path 56. At an upstream end 58 of first sterile fluid path 54 is a first needle 60, and at an upstream end 62 of second sterile fluid path 56 is a second needle 64. First sterile fluid path 54 and second sterile fluid path 56 share a common downstream end 66, at which is disposed injection assembly 30. FIG. 2A shows first therapeutic substance reservoir 50 and second therapeutic substance reservoir 52 ready to be inserted into therapeutic substance delivery device 20. When first prefilled therapeutic substance reservoir 50 and second prefilled therapeutic substance reservoir 52 are engaged with therapeutic substance delivery device 20, such as is shown in FIG. 2B, (a) a first disinfection chamber 68 is defined between first sterile fluid path 54 and first reservoir 50, and (b) a second disinfection chamber 70 is defined between second sterile fluid path 56 and second reservoir 52.

First needle 60 and second needle 64 are driven by control circuitry 38 to penetrate first disinfection chamber 68 and second disinfection chamber 70 respectively, and subsequently first reservoir 50 and second reservoir 52 respectively, such as is shown in FIG. 2C. Thereby a first fluid communication is established between first sterile fluid path 54 and first reservoir 50, and a second fluid communication is established between second sterile fluid path 56 and second reservoir 52. When activated by control circuitry 38, disinfection assembly 36, e.g., ultraviolet radiation source 37, (a) disinfects first disinfection chamber 68 prior to first needle 60 penetrating first disinfection chamber 68, and (b) disinfects second disinfection chamber 70 prior to second needle 64 penetrating second disinfection chamber 70. For example, ultraviolet radiation source 37 may emit ultraviolet radiation 42 through respective walls of first disinfection chamber 68 and second disinfection chamber 70. Within 5 minutes after activation, control circuitry 38 terminates the activation of disinfection assembly 36, and subsequently drives first needle 60 and second needle 64 to respectively penetrate first disinfection chamber 68 and second disinfection chamber 70 within 10 seconds after terminating the activation of disinfection assembly 36.

Typically, two valves are used to control fluid communication between the respective reservoirs and injection assembly 30. For example, a first sterile fluid path valve 72 may be disposed between first needle 60 and injection assembly 30 to control fluid communication between first reservoir 50 and injection assembly 30, and a second sterile fluid path valve 74 may be disposed between second needle 64 and injection assembly 30 to control fluid communication between second reservoir 52 and injection assembly 30.

Figure 2D:
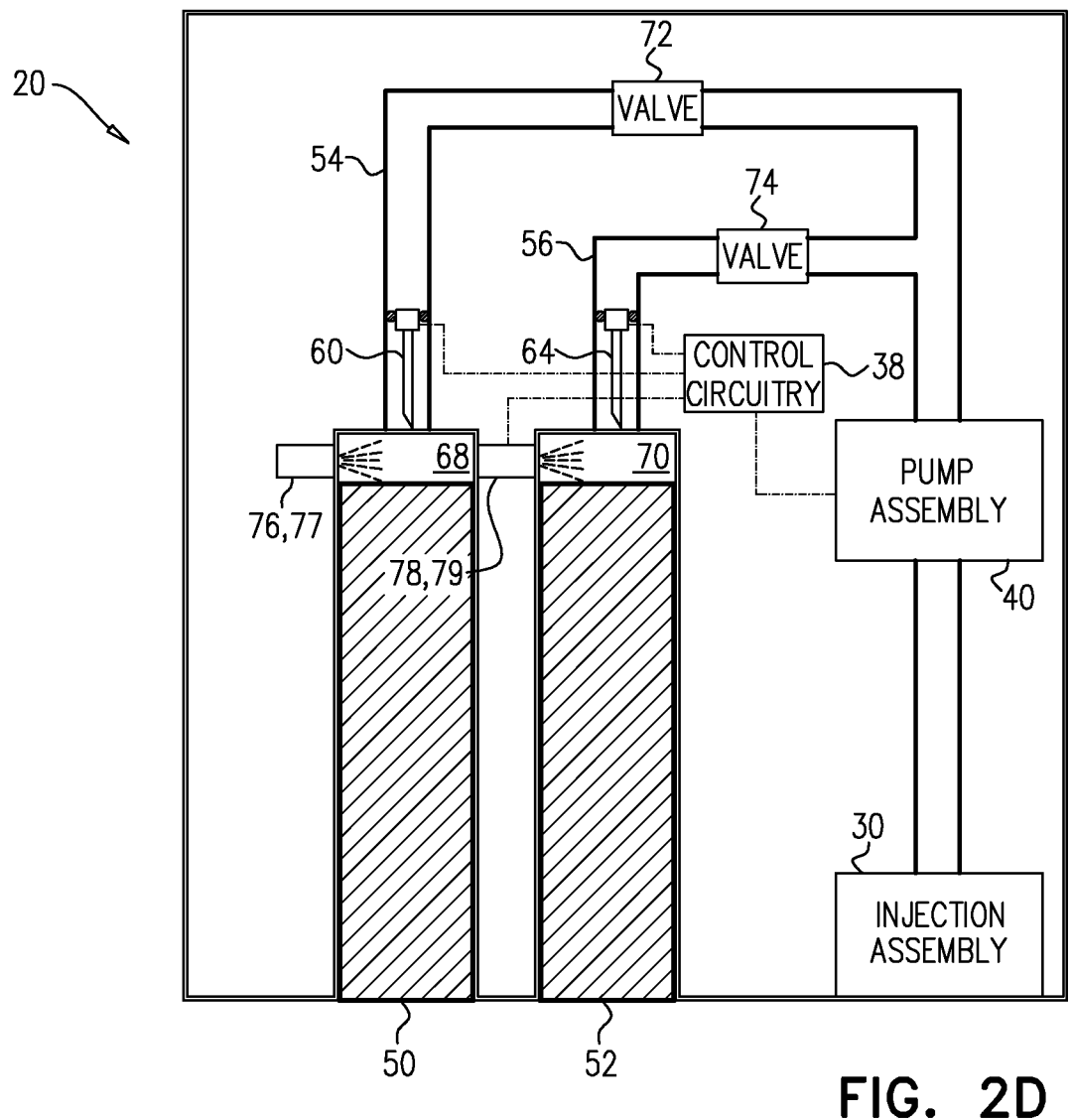
FIG. 2D is a schematic illustration of a therapeutic substance delivery device that includes two disinfection assemblies and is configured to engage with two prefilled therapeutic substance reservoirs, the reservoirs being shown engaged with the therapeutic substance delivery device, in accordance with some applications of the present invention.

Reference is now made to FIG. 2D, which is a schematic illustration of therapeutic substance delivery device 20 with two disinfection assemblies. For some applications, instead of using one disinfection assembly to disinfect both disinfection chambers 68 and 70, a first disinfection assembly 76, e.g., a first ultraviolet radiation source 77, disinfects first disinfection chamber 68, and a second disinfection assembly 78, e.g., a second ultraviolet radiation source 79, disinfects second disinfection chamber 70. Control circuitry 38 may activate the first and second disinfection assemblies simultaneously or independently of each other. When first disinfection assembly 76 and second disinfection assembly 78 are activated independently, control circuitry 38 (a) drives first needle 60 to penetrate first disinfection chamber 68 within 10 seconds after terminating the activation of first disinfection assembly 76, and (b) drives second needle 64 to penetrate second disinfection chamber 70 within 10 seconds after terminating the activation of second disinfection assembly 78. All features of disinfection assembly 36 described hereinabove with reference to FIGS. 1A-C and FIGS. 2A-C may apply to first disinfection assembly 76 and second disinfection assembly 78.

Figure 3A:
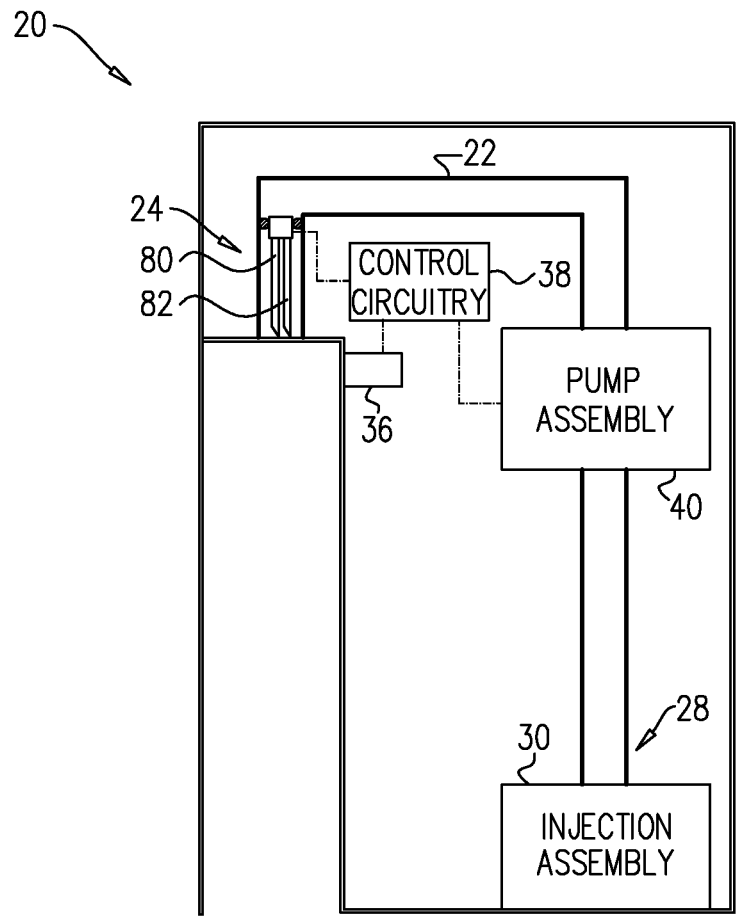
FIG. 3A is a schematic illustration of a therapeutic substance delivery device that includes a disinfection assembly and two needles, and is configured to engage with a prefilled therapeutic substance reservoir, the reservoir being shown outside the therapeutic substance delivery device, in accordance with some applications of the present invention.
Figure 3A:
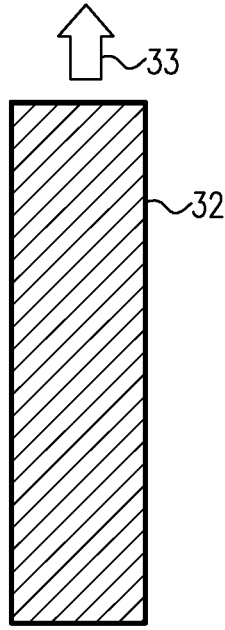
Figure 3B:
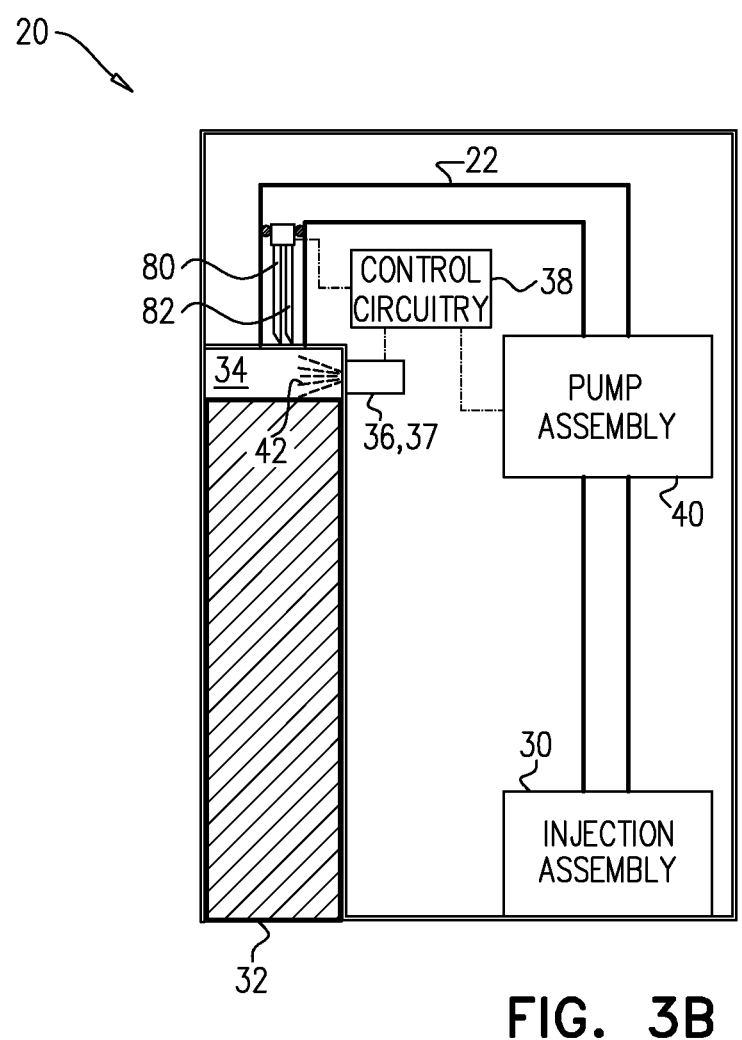
FIG. 3B is a schematic illustration of the therapeutic substance delivery device of FIG. 3A with the prefilled therapeutic substance reservoir engaged with the therapeutic substance delivery device, in accordance with some applications of the present invention.
Figure 3C:
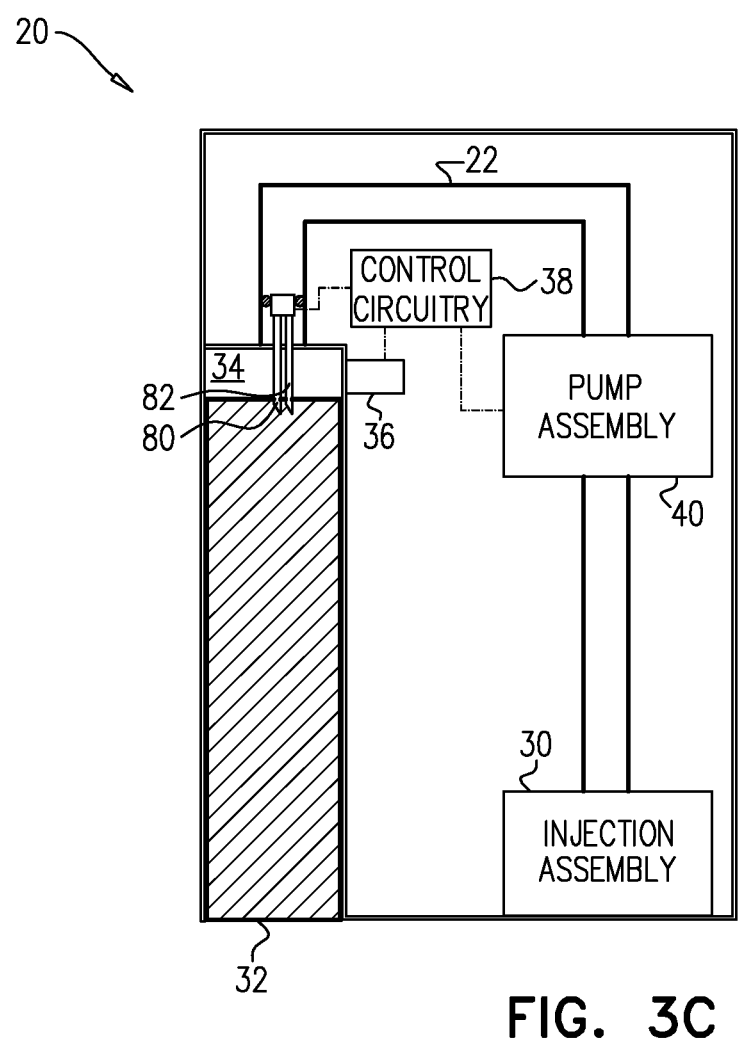
FIG. 3C is a schematic illustration of the therapeutic substance delivery device of FIGS. 3A-B, showing establishment of fluid communication by penetration of the reservoir with the two needles, in accordance with some applications of the present invention.

Reference is now made to FIGS. 3A-C, which are schematic illustrations of therapeutic substance delivery device 20 configured to engage with prefilled therapeutic substance reservoir 32, in accordance with some applications of the present invention. For some applications, to increase the rate of flow of the therapeutic substance, more than one needle may be used to establish fluid communication between reservoir 32 and sterile fluid path 22. For example, a first needle 80 and a second needle 82 may be disposed at upstream end 24 of sterile fluid path 22. Control circuitry 38 activates disinfection assembly 36, e.g., ultraviolet radiation source 37, to disinfect disinfection chamber 34 (FIG. 3B), terminates the activation of disinfection assembly 36 within 5 minutes, and subsequently drives first needle 80 and second needle 82 to penetrate disinfection chamber 34 and subsequently reservoir 32 (FIG. 3C) within 10 seconds after terminating the activation of disinfection assembly 36. Fluid communication is thereby established via first needle 80 and second needle 82.

Reference is now made to FIGS. 4A-B. FIG. 4A is a schematic illustration of therapeutic substance delivery device 20 showing a sensor 84, e.g., an ultraviolet sensor, disposed within disinfection chamber 34, and FIG. 4B is a graph showing a model that may be used to determine disinfection time based on measurements taken by sensor 84, in accordance with some applications of the present invention. Different UV LED's may emit UV radiation at different intensities; therefore, in order to improve efficiency and efficacy of the disinfection the inventors have realized that it is useful for control circuitry 38 to receive an indication of the UV intensity within disinfection chamber 34 after activation of the UV LED. Thus, for some applications, in order to improve efficiency and efficacy of the disinfection, control circuitry 38 of therapeutic substance delivery device 20 uses a closed-loop feedback system to determine how long disinfection assembly 36, e.g., ultraviolet radiation source 37, should be active for, i.e., an amount of time between activation of disinfection assembly 36 and termination of disinfection assembly 36.

For some applications, after activation of disinfection assembly 36, e.g., ultraviolet radiation source 37, sensor 84 measures the intensity of the ultraviolet radiation within disinfection chamber 34. Control circuitry 38 receives the value of the measured UV intensity and, based on the measured UV intensity, (i) determines a disinfection time and (ii) terminates the irradiation of disinfection chamber 34 at the determined time. For some applications, control circuitry 38 may determine the disinfection time by using a formula or a look-up table. After termination of the activation of disinfection assembly 36, control circuitry 38 drives needle 26 to penetrate disinfection chamber 34 and subsequently reservoir 32, as described hereinabove. In the example shown in FIG. 4B, arrow 86 points to a position on the graph indicating a value of the measured UV intensity. Arrow 88 points to a corresponding value of the determined disinfection time, after which control circuitry 38 will terminate the irradiation of disinfection chamber 34. As described hereinabove termination of the activation of disinfection assembly 36 typically occurs within 5 minutes, e.g., within 10 seconds, after activating disinfection assembly 36.

For some applications, disinfection assembly 36 may be a heat source, as described hereinabove. Sensor 84 may be a temperature sensor that measures a temperature of disinfection chamber 34 after activation of the heat source. Control circuitry 38 receives the measured temperature value from the temperature sensor and, based on the measured temperature value, (i) determines a disinfection time, e.g., by using a formula or a look-up table, and (ii) terminates the heat source at the determined time. After termination of activation of the heat source, control circuitry 38 drives needle 26 to penetrate disinfection chamber 34 and subsequently reservoir 32, as described hereinabove.

Figure 5:
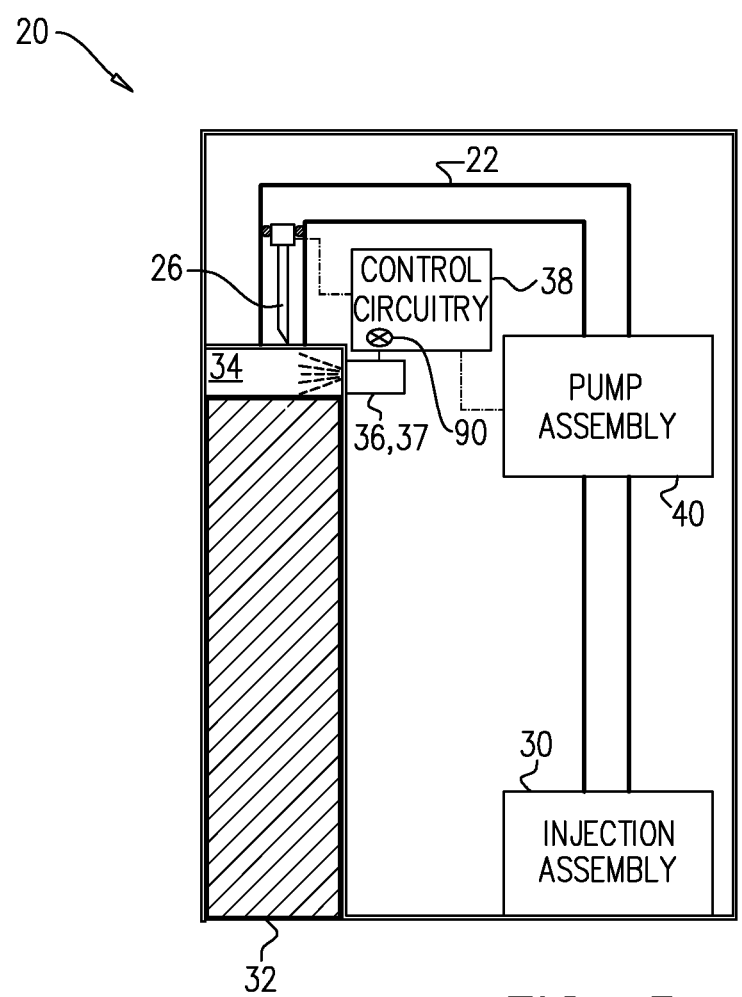
FIG. 5 is a schematic illustration of a therapeutic substance delivery device that includes a disinfection assembly, showing a current meter coupled to the control circuitry, in accordance with some applications of the present invention.

Reference is now made to FIG. 5, which is a schematic illustration of therapeutic substance delivery device 20 showing a current meter 90 coupled to control circuitry 38, in accordance with some applications of the present invention. For some applications, measuring the current running through the UV LED may be indicative of the UV radiation within disinfection chamber 34. Current meter 90 may measure the current indicative of the UV radiation within disinfection chamber 34, e.g., current meter 90 may measure the current going through a resistor within control circuitry 38 that is indicative of the UV radiation within disinfection chamber 34. After measuring the current indicative of the UV intensity within disinfection chamber 34, control circuitry 38 determines a disinfection time, e.g., by using a formula or a look-up table, and terminates the activation of ultraviolet radiation source 37 after the determined time. After termination of disinfection assembly 36, control circuitry 38 drives needle 26 to penetrate disinfection chamber 34 and subsequently reservoir 32, as described hereinabove.

Similarly, for some applications, such as when disinfection assembly 36 is a heat source, measuring the current running through the heat source may be indicative of the temperature of disinfection chamber 34. Current meter 90 may measure the current indicative of the temperature of disinfection chamber 34, e.g., current meter 90 may measure the current going through a resistor within control circuitry 38 that is indicative of the temperature of disinfection chamber 34. After measuring the current indicative of the temperature of disinfection chamber 34, control circuitry 38 determines a disinfection time, e.g., by using a formula or a look-up table, and terminates the activation of the heat source at the determined time. After termination of the heat source, control circuitry 38 drives needle 26 to penetrate disinfection chamber 34 and subsequently reservoir 32, as described hereinabove.

It is noted that therapeutic substance reservoir 32 is described hereinabove, for some applications, as being a prefilled therapeutic substance reservoir 32. For example, a user may purchase therapeutic substance reservoir 32 already filled with a particular therapeutic substance. Alternatively, the user may purchase therapeutic substance reservoir 32 empty, and subsequently the user may fill the therapeutic substance reservoir.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
   using a disinfection assembly disposed within a therapeutic substance delivery device, disinfecting a disinfection chamber that is defined between (i) a prefilled therapeutic substance reservoir and (ii) a sterile fluid path disposed within the therapeutic substance delivery device,
   the sterile fluid path comprising a needle at an upstream end of the sterile fluid path and an injection assembly at a downstream end of the sterile fluid path; and
   penetrating the disinfection chamber and then the reservoir with the needle,
   the disinfecting occurring (a) subsequently to the prefilled therapeutic substance reservoir being engaged with the therapeutic substance delivery device and (b) prior to the penetrating of the disinfection chamber and then the reservoir with the needle.

2. The method according to claim 1, wherein the step of disinfecting the disinfection chamber is performed following a user of the therapeutic substance delivery device engaging the prefilled therapeutic substance reservoir with the therapeutic substance delivery device, wherein the disinfection chamber is defined when the prefilled therapeutic substance reservoir becomes engaged with the therapeutic substance delivery device.

3. The method according to claim 1, wherein the step of disinfecting the disinfection chamber is performed following a user of the therapeutic substance delivery device removing the therapeutic substance delivery device from commercial packaging, wherein the prefilled therapeutic substance reservoir and the therapeutic substance delivery device are engaged with one another inside the commercial packaging.

4. The method according to claim 1, wherein disinfecting the disinfection chamber comprises activating the disinfection assembly and subsequently terminating the activation of the disinfection assembly, and wherein penetrating the disinfection chamber comprises penetrating the disinfection chamber within 10 seconds after terminating the activation of the disinfection assembly.

5. The method according to claim 1, wherein disinfecting the disinfection chamber comprises activating the disinfection assembly and terminating activation of the disinfection assembly within 5 minutes after activating the disinfection assembly.

6. The method according to claim 1, wherein disinfecting the disinfection chamber comprises irradiating the disinfection chamber with ultraviolet radiation.

7. The method according to claim 6, wherein irradiating the disinfection chamber comprises irradiating the disinfection chamber with ultraviolet radiation at a power level of 1-200 mW.

8. The method according to claim 6, wherein irradiating the disinfection chamber comprises irradiating the disinfection chamber with ultraviolet radiation at a wavelength of 100-400 nm.

9. The method according to claim 6, wherein irradiating the disinfection chamber comprises irradiating the disinfection chamber with ultraviolet light using an ultraviolet light emitting diode.

10. The method according to claim 6, further comprising:
    subsequently to irradiating the disinfection chamber with the ultraviolet light, measuring a value indicative of intensity of the ultraviolet radiation within the disinfection chamber; and
    terminating the irradiation of the disinfection chamber at a time determined based on the measured value.

11. The method according to claim 10, wherein measuring the value indicative of intensity of the ultraviolet radiation comprises measuring the intensity of the ultraviolet radiation within the disinfection chamber using an ultraviolet sensor disposed within the disinfection chamber.

12. The method according to claim 10, wherein (a) irradiating the disinfection chamber with ultraviolet radiation comprises activating an ultraviolet light emitting diode (UV LED) and (b) measuring the value indicative of intensity of the ultraviolet radiation comprises measuring a current input to the UV LED.

13. The method according to claim 1, wherein disinfecting the disinfection chamber comprises heating the disinfection chamber.

14. The method according to claim 13, wherein heating the disinfection chamber comprises heating the disinfection chamber to a temperature of 40-300 degrees Celsius.

15. The method according to claim 1, wherein disinfecting the disinfection chamber comprises releasing a disinfectant fluid into the disinfection chamber.

16. The method according to claim 1, wherein disinfecting the disinfection chamber comprises disinfecting the disinfection chamber within 5 minutes prior to penetrating the disinfection chamber and subsequently the reservoir with the needle.

17. The method according to claim 16, wherein disinfecting the disinfection chamber comprises disinfecting the disinfection chamber at least 1 month following engagement of the prefilled therapeutic substance reservoir with the therapeutic substance delivery device.

18. The method according to claim 17, wherein disinfecting the disinfection chamber comprises disinfecting the disinfection chamber at least 6 months following engagement of the prefilled therapeutic substance reservoir with the therapeutic substance delivery device.

19. The method according to claim 16, wherein the disinfecting of the disinfection chamber is at least a second disinfecting of the disinfection chamber, a first disinfecting of the disinfection chamber occurring prior to the therapeutic substance delivery device being packaged for commercial sale.

20. The method according to claim 19, further comprising disinfecting the disinfection chamber at least one time between the first disinfecting of the disinfection chamber and the at least a second disinfecting of the disinfection chamber.

* * * * *